US012714784B2

(12) United States Patent
Jang et al.

(10) Patent No.: US 12,714,784 B2
(45) Date of Patent: Aug. 25, 2026

(54) WEARABLE RINGER DEVICE

(71) Applicants: Kil Dong Jang, Cheongju-si (KR); Jeong Bin Park, Seoul (KR); Woo Jin Jeong, Goyang-si (KR)

(72) Inventors: Kil Dong Jang, Cheongju-si (KR); Jeong Bin Park, Seoul (KR); Woo Jin Jeong, Goyang-si (KR)

(73) Assignees: Kil Dong Jang, Cheongju-si (KR); Jeong Bin Park, Seoul (KR); Woo Jin Jeong, Goyang-si (KR)

( * ) Notice: Subject to any disclaimer, the term of this patent is extended or adjusted under 35 U.S.C. 154(b) by 438 days.

(21) Appl. No.: 18/556,155

(22) PCT Filed: Apr. 22, 2022

(86) PCT No.: PCT/KR2022/005806
§ 371 (c)(1),
(2) Date: Oct. 19, 2023

(87) PCT Pub. No.: WO2022/225371
PCT Pub. Date: Oct. 27, 2022

(65) Prior Publication Data

US 2024/0226422 A1 Jul. 11, 2024

(30) Foreign Application Priority Data

Apr. 22, 2021 (KR) ........................ 10-2021-0052420

(51) Int. Cl.
*A61M 5/142* (2006.01)
*A61M 5/145* (2006.01)

(52) U.S. Cl.
CPC ........ *A61M 5/14244* (2013.01); *A61M 5/145* (2013.01); *A61M 2005/14506* (2013.01)

(58) Field of Classification Search
CPC .............. A61M 5/14244; A61M 5/145; A61M 2005/14506; A61M 5/142
See application file for complete search history.

(56) References Cited

U.S. PATENT DOCUMENTS 4,447,232 A * 5/1984 Sealfon ................ A61M 5/148 604/134
6,871,759 B2 3/2005 Rake et al.

FOREIGN PATENT DOCUMENTS

JP 2001-170175 6/2001
KR 20-2006-0000071 4/2006
(Continued)

OTHER PUBLICATIONS

PCT International Search Report for International Application No. PCT/KR2022/005806, mailed Aug. 12, 2022.
(Continued)

*Primary Examiner* — Bradley J Osinski

(57) ABSTRACT

The disclosed invention relates to a wearable intravenous drip device comprising: a first plate; at least one static load spring mounted on the first plate; a second plate to which a free end of a leaf spring wound around a drum of the static load spring is fixed, and which is disposed to face the first plate; and an upper arm loading part coupled to the second plate, wherein the static load springs apply elastic force causing a relative extension/contraction movement to be generated with respect to the first plate and the second plate, and the elastic force of the static load springs is constant regardless of the displacement of the leaf spring.

8 Claims, 4 Drawing Sheets

(56) References Cited

FOREIGN PATENT DOCUMENTS

| | | |
|---|---|---|
| KR | 20-2015-0007772 | 8/2016 |
| KR | 10-2015-0180828 | 5/2017 |
| KR | 20-2016-7000009 | 11/2019 |
| KR | 10-2021-0052420 | 2/2022 |

OTHER PUBLICATIONS

Office Action(Notice of Allowance) for Korea Patent Application No. 10-2021-0052420, mailed Jan. 5, 2022.

* cited by examiner

【Fig. 1】
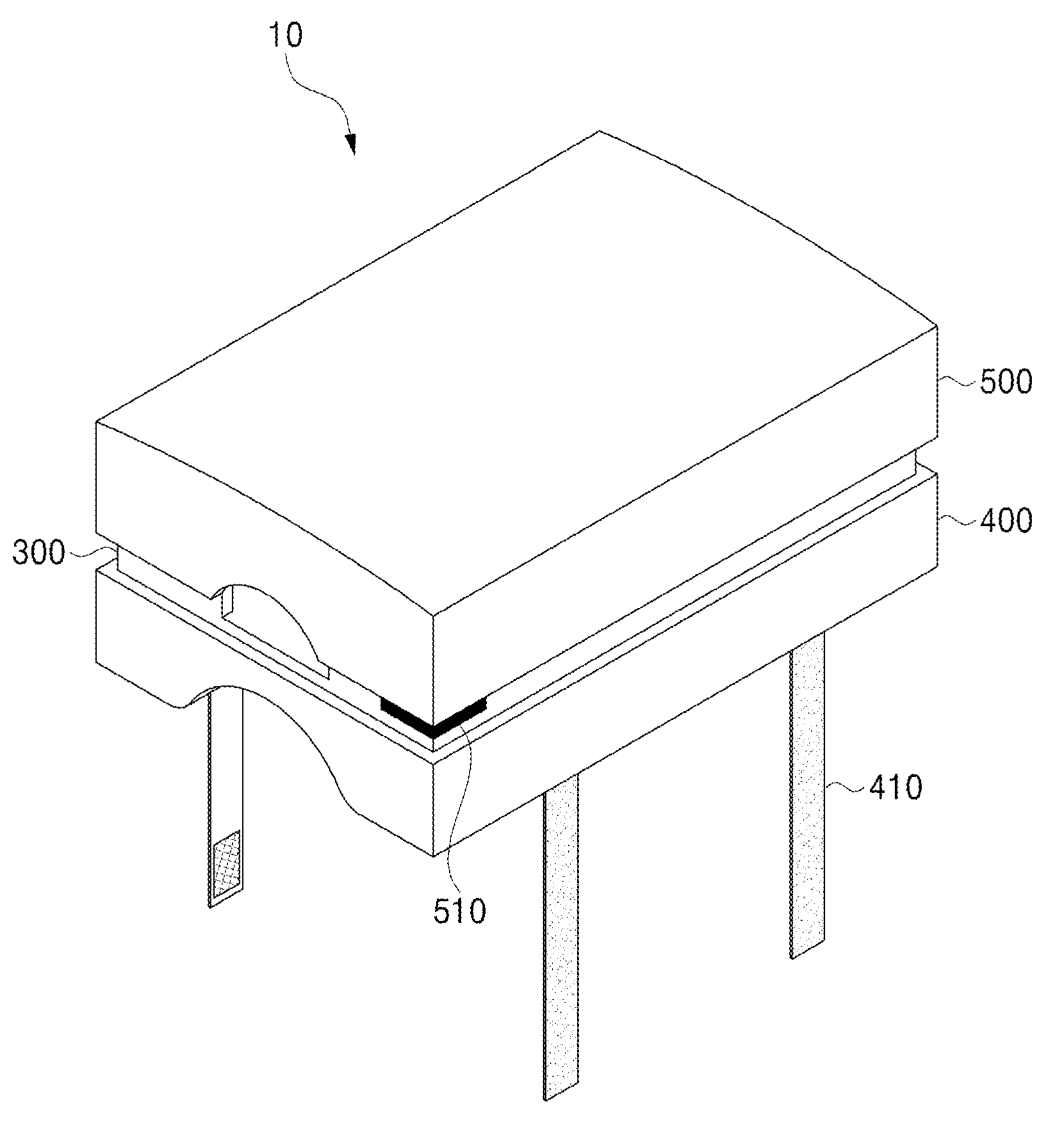

【Fig. 2】
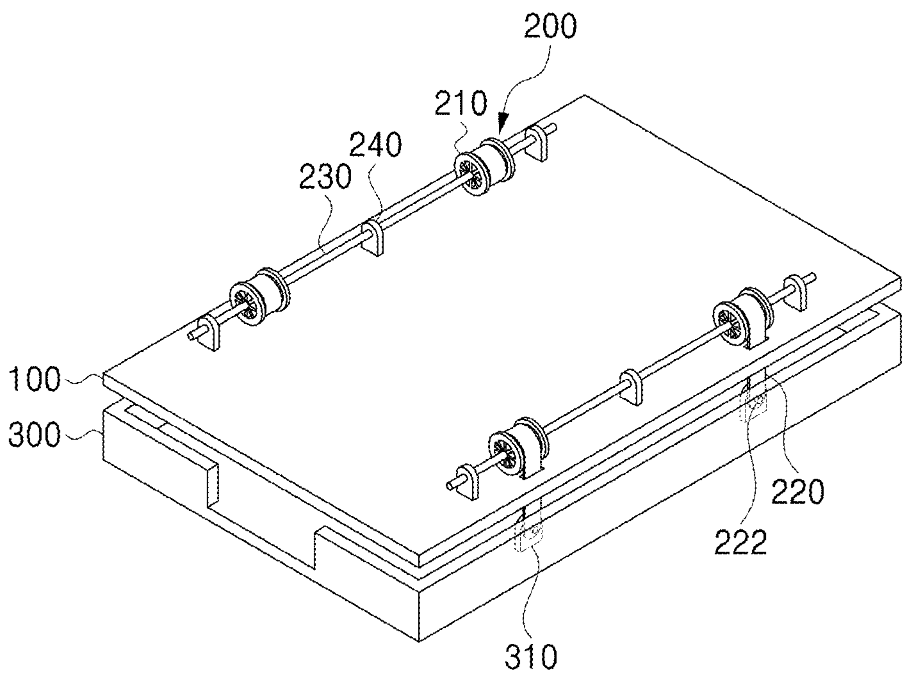

【Fig. 3】
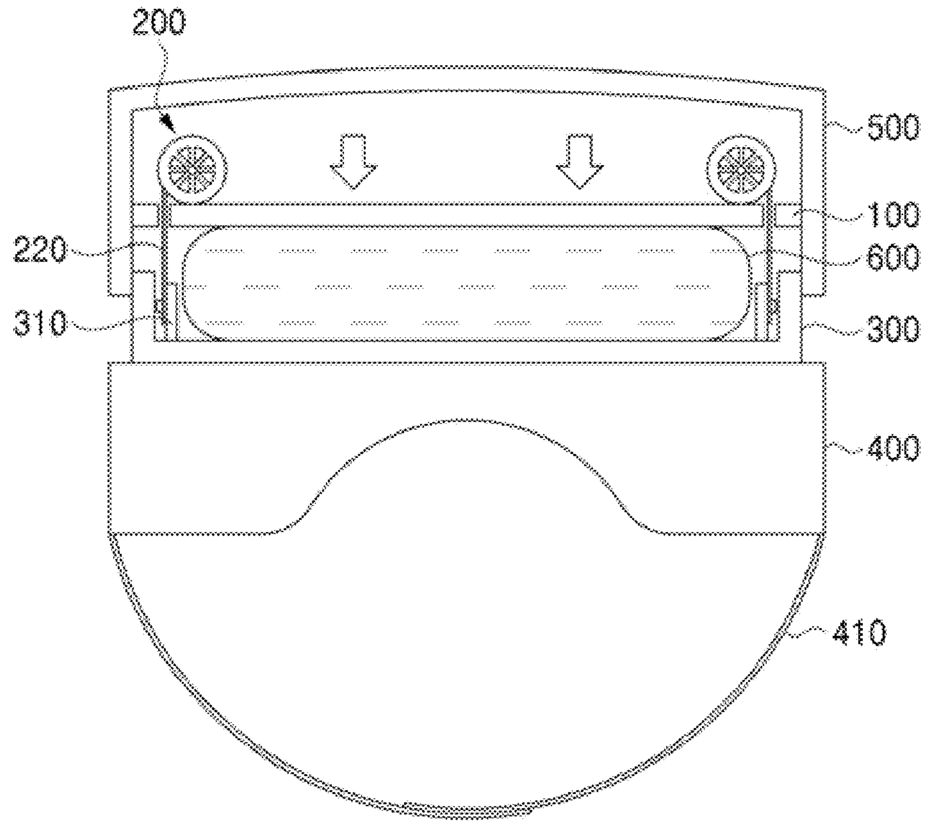

【Fig. 4】
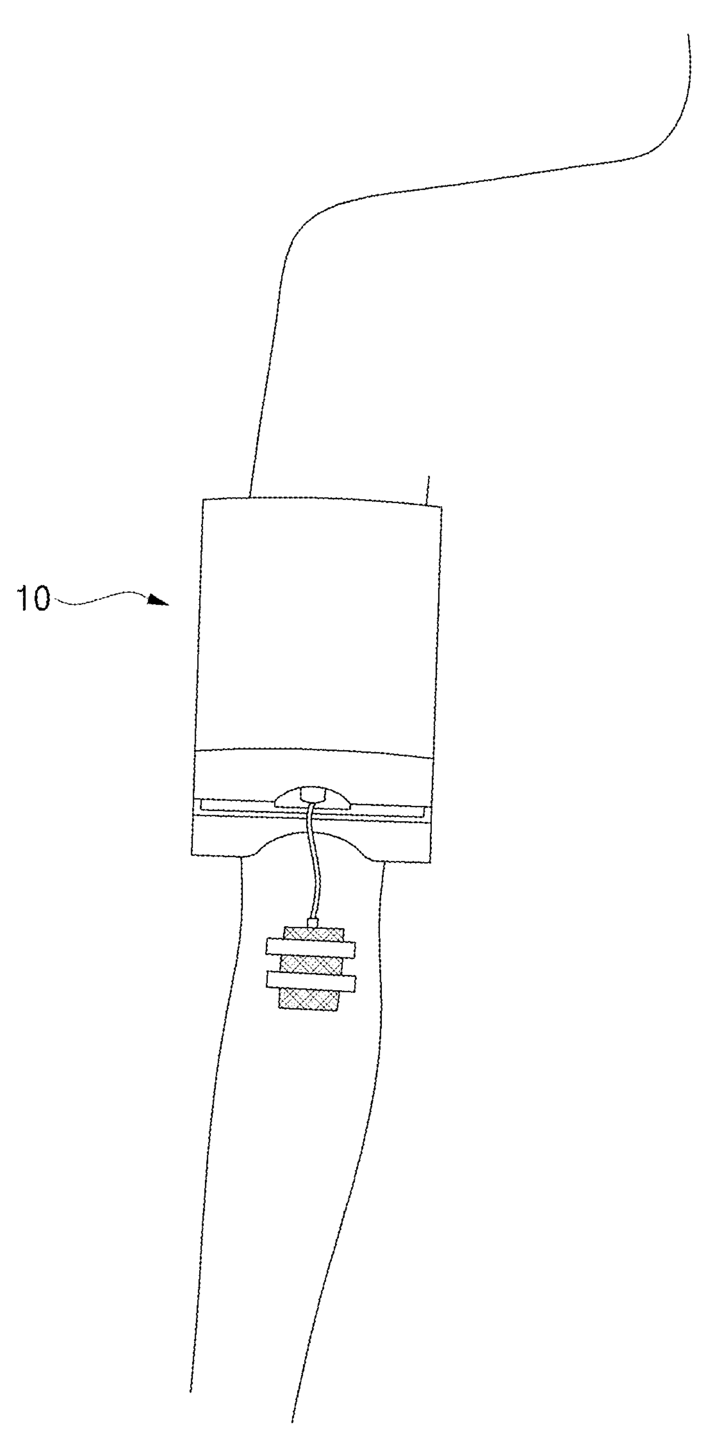

WEARABLE RINGER DEVICE

TECHNICAL FIELD

The present invention relates to a wearable intravenous drip device that allows a user to move freely while wearing it.

BACKGROUND ART

In order to administer an intravenous fluid to a patient, a mobile IV stand is required to hold a fluid bag at a height. A mobile IV stand with wheels helps a patient receiving an intravenous fluid move short distances.

However, the mobile IV stand has the disadvantage of not being very convenient to use because it imposes certain restrictions on the activities of a user. In other words, wheels of the mobile IV stand often bump into feet, which is inconvenient, and it is difficult to take the mobile IV stand into bathrooms or other narrow places. Additionally, there is a risk of safety accidents occurring when using an elevator, such as a wheel getting caught in the gap between the floor and the elevator car or the mobile IV stand falling over. Also, when using the stairs, most patients have to manually the long and heavy IV stand up and down the stairs, which causes a lot of inconvenience.

The reason the mobile IV stand must be long is because the height of an intravenous fluid must be higher than the position of a needle inserted into a blood vessel so that the intravenous fluid is injected by pressure generated by a difference in height of the fluid. If the height of the intravenous fluid is lower than the needle, backflow of blood may occur, which can be dangerous.

An intravenous fluid supply device with a built-in electronically controlled pump may be a solution to overcome the limitations of such a mobile IV stand using gravity, but it is difficult to secure mobility because the device usually uses an external power source. In addition, because the intravenous fluid supply device is expensive, it is difficult to provide it to many patients. Furthermore, because the intravenous fluid supply device weighs several kilograms, it is not suitable for carrying around.

DISCLOSURE OF THE INVENTION

Technical Problem

The purpose of the present invention is to provide a wearable intravenous drip device, which can overcome the limitations of mobile IV stands using gravity, be manufactured inexpensively by not using an electronically controlled pump, and be formed with a light weight so that a user can wear it, thereby maximizing patient activity.

Technical Solution

The present invention relates to a wearable intravenous drip device, including: a first plate; at least one static load spring mounted on the first plate; a second plate to which a free end of a leaf spring wound around a drum of the static load spring is fixed and which is disposed to face the first plate; and an upper arm loading part coupled to the second plate, wherein the static load spring exerts elastic force that causes a relative extension/contraction movement with respect to the first plate and the second plate, and elastic force of the static load spring is constant regardless of displacement of the leaf spring.

Herein, a shaft is provided on the first plate so as to be rotatably supported by a support, and the shaft serves as a rotation axis for the drum of the static load spring.

In addition, it may be preferable that the free end of the leaf spring is fixed to the second plate in a direction parallel to the displacement of the extension/contraction movement that occurs between the first plate and the second plate.

Moreover, it may be preferable that when the first plate and the second plate are at a minimum distance, the leaf spring of the static load spring reaches a maximum load.

Furthermore, according to an embodiment of the present invention, it may be preferable that a cover for protecting the static load spring is provided on the first plate and a distance with respect to the second plate can be artificially increased by moving the first plate by applying force to the cover.

Accordingly, an IV bag can be inserted into a space created by increasing the distance of the first plate with respect to the second plate.

In addition, an indicator can be provided to indicate that the first plate and the second plate are at the minimum distance.

Moreover, the upper arm loading part is provided with a fixing band of which length is adjustable.

Advantageous Effects of the Invention

The wearable intravenous drip device of the present invention is composed of a simple structure using a mechanical static load spring so that it can secure the economic feasibility of replacing existing IV devices and convenience is also excellent as existing IV sets can be used as is. In other words, the wearable intravenous drip device of the present invention satisfies all aspects of efficiency, cost-effectiveness, and convenience, and is also advantageous for commercialization.

In addition, the wearable intravenous drip device of the present invention has a simple structure and is not heavy, so there is no burden for a patient to operate while fixing it on his or her upper arm. Therefore, compared to the conventional mobile drip device with wheels, the patient is guaranteed much more freedom of movement, and in this sense, the present invention is very suitable for use as a wearable intravenous drip device.

The effects of the present invention are not limited to the effects mentioned above, and other effects not mentioned will be clearly understood by those skilled in the art from the detailed description below.

BRIEF DESCRIPTION OF THE INVENTION

FIG. 1 is a view illustrating an overall appearance of a wearable intravenous drip device according to the present invention.

FIG. 2 is a view illustrating a static load pressurization structure included in the wearable intravenous drip device.

FIG. 3 is a view illustrating an operating state of a static load spring.

FIG. 4 is a view illustrating a state in which the wearable intravenous drip device according to the present invention is used.

MODE FOR INVENTION

Hereinafter, preferred embodiments of the present invention will be described in detail with reference to the accompanying drawings. The advantages and features of the present invention and methods for achieving them will become clear by referring to the embodiments described in detail below along with the accompanying drawings. However, the present invention is not limited to the embodiments disclosed below and may be implemented in various different forms. The embodiments are provided solely to ensure complete disclosure of the present invention and to fully inform those skilled in the art of the scope of the invention, and the invention is defined only by the scope of the claims. Like reference numerals refer to like elements throughout the specification.

Unless otherwise defined, all terms used herein, including technical and scientific terms, may be used to have meaning that can be commonly understood by those skilled in the art to which the present invention belongs. Additionally, terms defined in commonly used dictionaries are not to be interpreted ideally or excessively unless specifically defined. The terms used herein are used to describe embodiments and are not intended to limit the present invention. As used herein, the singular includes the plural, unless the context specifically dictates otherwise.

The expression “comprises” and/or “comprising” used herein in relation to a stated component, step, operation and/or element does not exclude the presence or addition of one or more other components, steps, operations and/or elements.

A wearable intravenous drip device 10 according to the present invention is a mechanical implementation of a conventional gravity-type intravenous fluid supply device. To help understand the present invention, the principle of supplying an intravenous fluid using gravity in a conventional device is briefly described.

The main principle of conventional intravenous fluid injection is the siphon principle. A siphon is a pipe that moves liquid from a high place to a low place by using atmospheric pressure. If the siphon is full of liquid, in order to maintain the pressure in the pipe, a net force acts from a high place to a low place, and this force is basically proportional to a fluid level difference and has constant magnitude. Therefore, regardless of the curve of the pipe, if there is a height difference between an IV bag and an IV needle (if the IV bag is higher), an intravenous fluid is injected due to the head difference.

In this gravity-type intravenous fluid supply device, an intravenous fluid is injected at a constant flow rate by applying static pressure due to the height difference between the IV bag and the IV needle. This gravity-type intravenous fluid supply device is simple but very effective. However, in order to inject an intravenous fluid, the IV bag must be placed above a certain height, so a stand such as a mobile IV stand is essential, which places many restrictions on patient’s activities.

The present invention was created to maintain a constant amount of fluid infusion by applying static pressure to an IV bag 600 without using gravity. In particular, efficiency, cost-effectiveness, and convenience are achieved by using a simplified mechanical device that does not employ an expensive electronically controlled pump, for example, a stepping motor and a control circuit thereof, and a power source. The wearable intravenous drip device 10 of the present invention will be described in detail as follows.

FIG. 1 is a view illustrating an overall appearance of the wearable intravenous drip device 10 according to the present invention, FIG. 2 is a view illustrating a static load pressurization structure included in the wearable intravenous drip device 10, and FIG. 3 is a view illustrating an operating state of a static load spring 200. The present invention will be described in detail with reference to the accompanying drawings.

The wearable intravenous drip device 10 of the present invention basically includes a first plate 100, a second plate 300, and a static load spring 200.

In the present invention, the first plate 100 and the second plate 300 act as pressure plates. An IV bag 600 with variable volume is inserted between the first plate 100 and the second plate 300, and compressive force is applied to the IV bag 600 by elastic force of springs fixed at both ends to the first plate 100 and the second plate 300, so that an intravenous fluid is injected. Herein, what is important herein is that an injection amount of an intravenous fluid is maintained constant only when compressive force applied to the IV bag 600 acts as a constant static load. To this end, the present invention uses the static load spring 200.

In typical mechanical springs, such as coil springs, elastic force is proportional to displacement according to Hooke’s law. In other words, if a general spring is applied, an injection amount is large when the IV bag 600 is full, and the injection amount gradually decreases as an intravenous fluid is injected and a volume of the IV bag 600 decreases. Therefore, the wearable intravenous drip device 10 of the present invention uses the static load spring 200 that generates uniform output (elastic force) regardless of displacement.

The static load spring 200 includes a leaf spring 220 wound around a drum 210. The leaf spring 220 wound around the drum 210 is wound with a certain curvature, and after reaching a maximum load, the leaf spring 220 outputs elastic force constantly no matter how much the displacement increases. The drum 210 of the static load spring 200 is provided with a shaft 230 inserted into the drum 210 so as to rotate around the shaft 230, wherein if one of the drum 210 and a free end 222 of the leaf spring 220 is fixed and a load is applied to the other, a constant static load is output. For example, if a static load spring is mounted on a glass door, it is possible to obtain the effect of moving the glass door at a constant speed when the glass door is opened and closed.

FIG. 2 shows a structure in which the static load spring 200 is mounted on the wearable intravenous drip device 10 of the present invention. At least one static load spring 200 is mounted on the first plate 100, and the free end 222 of the leaf spring 220 wound around the drum 210 is fixed to the second plate 300 disposed to face the first plate 100. The shaft 230 is provided on the first plate 100 and is rotatably supported by a support 240, and the shaft 230 is coupled to the drum 210 of the static load spring 200 so as to act as a rotation axis.

Owing to the structure, in which the drum 210 of the static load spring 200 is fixed to the first plate 100, and the free end 222 of the leaf spring 220 is fixed to the second plate 300, a static load is applied between the first plate 100 and the second plate 300 by the static load spring 200, so that the first plate 100 and the second plate 300 can carry out extension/retraction movement relative to each other. In other words, when the IV bag 600 with variable volume is inserted between the first plate 100 and the second plate 300, a certain load generated by the static load spring 200 acts as a compressive force on the IV bag 600, and thus the intravenous fluid discharged from the IV bag 600 is maintained at a constant flow rate. Through this static load pressurization structure, the wearable intravenous drip device 10 of the present invention can inject an intravenous fluid by using mechanical elastic force instead of gravity.

An appropriate number of static load springs 200 is selected in consideration of a required output, that is, an injection amount of an intravenous fluid. Since a maximum injection flow rate of an intravenous fluid is dependent on an output of the static load spring 200, it is necessary to install a sufficient number of static load springs 200 so as to respond to various clinical cases. When a plurality of static load springs 200 are provided, it is preferable that the static load springs 200 are arranged symmetrically so that compressive force is applied evenly to the IV bag 600.

In addition, referring to FIG. 2 and FIG. 3, the free end 222 of the leaf spring 220 is fixed to the second plate 300 in a direction parallel to the displacement of the extension/retraction movement that occurs between the first plate 100 and the second plate 300. This is because an originally intended static load can be accurately implemented only when the leaf spring 220 wound around the drum 210 moves in a flat state.

Additionally, it may be preferable that the leaf spring 220 of the static load spring 200 is designed to reach the maximum load when the first plate 100 and the second plate 300 are at a minimum distance. This is to ensure that an injection amount of the intravenous fluid remains constant until the IV bag 600 is emptied, that is, from the beginning to the end of the injection of an intravenous fluid injection. In the case of the static load spring 200 illustrated, a maximum output is usually reached when the drum 210 rotates ½. Therefore, the condition is met if the drum 210 is designed to rotate ½ or more when the leaf spring 220 of the static load spring 200 in a neutral state is pulled and connected to a fixing part 310 of the second plate 300.

Meanwhile, Referring to FIG. 4, the wearable intravenous drip device 10 of the present invention is used by wearing the device 10 on a patient's upper arm, specifically, the upper arm where an intravenous fluid is injected. To this end, the second plate 300 is provided with an upper arm loading part 400 which can be fitted around the upper arm, and the upper arm loading part 400 is provided with a fixing band 410 of which length is adjustable. It is appropriate that the upper arm loading part 400 is made of a material that provides adequate cushioning so as to avoid discomfort in use, and can form a concave curve to match the shape of an upper arm. Insomuch as the wearable intravenous drip device 10 tightened with the fixing band 410 has a simple structure, the wearable intravenous drip device 10 is not heavy, so it is not burdensome for a patient to be active while wearing and fixing the device 10 on an upper arm. Therefore, compared to the conventional mobile IV stand with wheels, the patient is guaranteed much greater freedom of movement, and in this sense, the present invention can be called an excellent wearable intravenous drip device 10.

Meanwhile, the present invention may further include several components for convenience of use.

For example, according to an embodiment of the present invention, a cover 500 that protects the static load spring 200 may be provided on the first plate 100. The purpose of the cover 500 is to protect the static load spring 200, but in terms of use, it also functions as a gripping part that can provide strength so that the IV bag 600 can be easily inserted between the first and second plates 100 and 300. In other words, it is possible to artificially increase the distance to the second plate 300 by applying force to the cover 500 and lifting the first plate 100, and the IV bag 600 can be easily placed in thus open space between the first plate 100 and the second plate 300.

Furthermore, if the first plate 100 and the cover 500 are made of a transparent material, it is possible to check how much the IV fluid remains by looking at the IV bag 600 inside. However, if the first plate 100 and the cover 500 are made of an opaque material for the purpose of protecting privacy, blocking ultraviolet rays or the like, it may become difficult to check a remaining amount of the IV fluid. Therefore, the present invention may be provided with an indicator 510 that indicates that the first plate 100 and the second plate 300 are at a minimum distance. The indicator 510 refers to an indicator such as a scale for indicating that the first plate 100 and the second plate 300 are at a minimum distance, that is, the IV bag 600 is empty. When the first plate 100 lowers and thus matches the indicator 510 displayed on the second plate 300 or is obscured from view, a user can immediately recognize that the IV bag 600 is empty and convenience of use is improved.

Although the embodiments of the present invention have been described above with reference to the accompanying drawings, a person skilled in the art to which the present invention belongs will understand that the present invention can be implemented in other specific forms without changing the technical idea or essential features of the present invention. Therefore, the embodiments described above should be understood in all respects as illustrative and not restrictive.

The invention claimed is:

1. A wearable intravenous drip device comprising:

a first plate;

at least one static load spring mounted on the first plate;

a second plate to which a free end of a leaf spring wound around a drum of the static load spring is fixed and which is disposed to face the first plate; and an upper arm loading part coupled to the second plate, wherein the static load spring applies elastic force causing a relative extension/contraction movement to be generated with respect to the first plate and the second plate, and elastic force of the static load spring is constant regardless of displacement of the leaf spring.

2. The device according to claim 1, wherein a shaft is provided on the first plate so as to be rotatably supported by a support, and the shaft serves as a rotation axis for the drum of the static load spring.

3. The device according to claim 1, wherein the free end of the leaf spring is fixed to the second plate in a direction parallel to the displacement of the extension/contraction movement that occurs between the first plate and the second plate.

4. The device according to claim 3, wherein when the first plate and the second plate are at a minimum distance, the leaf spring of the static load spring reaches a maximum load.

5. The device according to claim 1, wherein a cover for protecting the static load spring is provided on the first plate, and a distance with respect to the second plate can be artificially increased by moving the first plate by applying force to the cover.

6. The device according to claim 5, wherein an IV bag can be inserted into a space created by increasing the distance of the first plate with respect to the second plate.

7. The device according to claim 1, wherein an indicator is provided to indicate that the first plate and the second plate are at the minimum distance.

8. The device according to claim 1, wherein the upper arm loading part is provided with a fixing band of which length is adjustable.

* * * * *